(12) United States Patent
Yoshida et al.

(10) Patent No.: US 12,201,358 B2
(45) Date of Patent: Jan. 21, 2025

(54) OCT DEVICE

(71) Applicant: NIDEK CO., LTD., Aichi (JP)

(72) Inventors: Taisei Yoshida, Aichi (JP); Hiroyuki Umano, Aichi (JP)

(73) Assignee: NIDEK CO., LTD., Aichi (JP)

( * ) Notice: Subject to any disclaimer, the term of this patent is extended or adjusted under 35 U.S.C. 154(b) by 481 days.

(21) Appl. No.: 17/671,821

(22) Filed: Feb. 15, 2022

(65) Prior Publication Data

US 2022/0313078 A1    Oct. 6, 2022

(30) Foreign Application Priority Data

Mar. 30, 2021 (JP) .................... 2021-058799
Mar. 30, 2021 (JP) .................... 2021-058800

(51) Int. Cl.
*A61B 3/10*     (2006.01)
*A61B 3/12*     (2006.01)
*G01B 9/02091*  (2022.01)

(52) U.S. Cl.
CPC ............... *A61B 3/102* (2013.01); *A61B 3/12* (2013.01); *G01B 9/02091* (2013.01)

(58) Field of Classification Search
CPC ......... A61B 3/102; A61B 3/12; A61B 3/1225; G01B 9/02091; G01B 9/02044; G01B 9/02064; G02B 27/10; G02B 27/30
See application file for complete search history.

(56) References Cited

U.S. PATENT DOCUMENTS

| 7,980,696 B1 | 7/2011 | Taki et al. |
| 2006/0066869 A1 | 3/2006 | Ueno et al. |
| 2006/0164639 A1 | 7/2006 | Horn et al. |

(Continued)

FOREIGN PATENT DOCUMENTS

| JP | 8-160276 A | 6/1996 |
| JP | 2006-101927 A | 4/2006 |

(Continued)

OTHER PUBLICATIONS

Communication dated Oct. 15, 2024, issued by the Japanese Patent Office in Japanese Application No. 2021-058800.

(Continued)

*Primary Examiner* — Cara E Rakowski
*Assistant Examiner* — Jennifer A Jones
(74) *Attorney, Agent, or Firm* — Sughrue Mion, PLLC

(57) ABSTRACT

An OCT device that selectively captures OCT data of a fundus of a subject eye and OCT data of an anterior segment of the subject eye. The OCT device includes a spectroscopic optical system that spectroscopically detects interference light between reference light and reflection light of measurement light irradiated on the subject eye. The spectroscopic optical system includes a collimating system that collimates the interference light, a spectrally dispersive element that spectrally disperses the collimated interference light for each spectral wavelength, an image formation system that forms an image of the interference light for each spectral wavelength on an imaging surface, and a light receiving element disposed on the imaging surface. An object-side focal length of the collimating system is shorter than an image-side focal length of the image formation system.

10 Claims, 9 Drawing Sheets

(56) References Cited

U.S. PATENT DOCUMENTS

| | | | |
|---|---|---|---|
| 2007/0030483 A1 | 2/2007 | Everett et al. | |
| 2009/0201467 A1* | 8/2009 | Smith | A61B 3/12 351/246 |
| 2010/0027857 A1 | 2/2010 | Wang | |
| 2011/0096291 A1 | 4/2011 | Buckland et al. | |
| 2011/0176107 A1 | 7/2011 | Yoshida et al. | |
| 2012/0062901 A1 | 3/2012 | Yoshida | |
| 2012/0274904 A1* | 11/2012 | Saito | A61B 3/12 351/221 |
| 2016/0081545 A1* | 3/2016 | Hauger | G01B 9/02035 351/221 |
| 2020/0397282 A1* | 12/2020 | Hirose | A61B 3/102 |
| 2022/0018712 A1* | 1/2022 | Hart | G01J 3/1804 |
| 2022/0079434 A1* | 3/2022 | Nishi | A61B 3/1025 |
| 2022/0236047 A1* | 7/2022 | Kamo | G01B 9/02083 |

FOREIGN PATENT DOCUMENTS

| | | | |
|---|---|---|---|
| JP | 2008-528953 A | | 7/2008 |
| JP | 2010-35949 A | | 2/2010 |
| JP | 2010-505127 A | | 2/2010 |
| JP | 2010-249584 A | | 11/2010 |
| JP | 2011-7775 A | | 1/2011 |
| JP | 2011-147612 A | | 8/2011 |
| JP | 2014-138904 A | | 7/2014 |
| JP | 2016028682 A | * | 3/2016 |
| JP | 2018-102677 A | | 7/2018 |
| JP | 2019-195378 A | | 11/2019 |

OTHER PUBLICATIONS

Communication dated Oct. 8, 2024, issued by the Japanese Patent Office in Japanese Application No. 2021-058799.

* cited by examiner

OCT DEVICE

CROSS-REFERENCE TO RELATED APPLICATION

This application claims priority from Japanese Patent Applications No. 2021-058799 filed on Mar. 30, 2021 and No. 2021-058800 filed on Mar. 30, 2021, the entire subject-matters of which are incorporated herein by reference.

TECHNICAL FIELD

The present disclosure relates to an OCT device.

BACKGROUND

In the field of ophthalmology, an optical coherence tomography (OCT), which is a device for capturing a tomographic image of a tissue of a subject eye, is known.

There are several methods for obtaining OCT data. Recently, devices using the spectral domain method (SD-OCT; Spectral-Domain OCT) are widely used in ophthalmic facilities.

The SD-OCT includes a wideband OCT light source and a spectroscopic optical system as a spectrometer. In SD-OCT, the interference light between reference light and reflection light of measurement light irradiated on the subject eye is detected as a spectral signal (spectral interference signal) by the spectroscopic optical system. As a result of processing the spectral interference signal, OCT data is acquired as information of the subject eye in the depth direction.

In such a case, the spectroscopic optical system includes, in addition to an optical element called a grating and a light receiving element such as a linear image sensor, a collimating system for collimating interference light and guiding the light to the grating, and an image formation system that provides an image of the interference light emitted from the grating on a light receiving element (refer to, for example, JP-A-2010-035949).

Further, there is a known a technique of selectively capturing images of a fundus OCT and an anterior segment OCT by switching an optical system. For example, JP-A-2014-138904 discloses an SD-OCT capable of easily capturing an image of the anterior segment OCT by attaching an adapter lens to the fundus OCT.

In the fundus tissue, for example, the retina, a large number of layer structures are formed within a range of only 0.2 to 0.3 mm. Therefore, a high-resolution imaging device is obtained. On the other hand, for the anterior segment OCT, a device having a wide imaging range suitable for grasping the shape of each part is suitable.

In a device for capturing images of the fundus OCT and the anterior segment OCT using the same spectrometer as in JP-A-2014-138904, there is no device on the market in which a sufficient imaging range in the depth direction called a depth range is ensured. Recently, the SD-OCT depth range of each company is mainly in a range of 2 mm to 2.3 mm, and the longest SD-OCT depth range is 3 mm by using Optvue's "AngioVue" (registered trademark). However, a sufficient imaging range is not ensured for the anterior segment. For example, in JP-A-2014-138904, only an image of a single portion of the anterior segment, such as a corneal scanning and a chamber angle scanning, is captured.

The present inventor has studied an SD-OCT optical system that is able to collectively capture images of a plurality of portions in the anterior segment in the imaging range in the depth direction and is able to ensure the resolution necessary for the fundus OCT. As a result, in the SD-OCT, in order to improve the resolution and the performance of the imaging range in the depth direction, it has been effective to increase the focal length of the image formation system as well as increase the number of pixels of the light receiving element.

By the way, since the spot size of the interference light is greater than the element size of the light receiving element, sensitivity attenuation is caused in accordance with the depth position. That is, the sensitivity is lower on the higher frequency side (depth position farther from the zero delay). The spot size is minimized in a case where a focal length of the collimating system is the same as or longer than a focal length of the image formation system. In such a case, sensitivity performance in the spectroscopic optical system is optimized.

Therefore, in the above-mentioned study, in a case where the focal length of the collimating system is increased in accordance with the image formation system, it is considered that the total length of the spectrometer is significantly enlarged.

SUMMARY

A technical object of the present disclosure is to provide a compact OCT device capable of satisfactorily capturing images of both the anterior segment OCT and the fundus OCT.

An aspect of the present disclosure is an OCT device that selectively captures OCT data of a fundus of a subject eye and OCT data of an anterior segment of the subject eye. The OCT device includes a spectroscopic optical system configured to spectroscopically detect interference light between reference light and reflection light of measurement light irradiated on the subject eye. The reflection light is the measurement light reflected from the subject eye. The spectroscopic optical system includes a collimating system configured to collimate the interference light, a spectrally dispersive element configured to spectrally disperse the collimated interference light for each spectral wavelength, an image formation system that configured to form an image of the interference light for each spectral wavelength on an imaging surface, and a light receiving element disposed on the imaging surface. An object-side focal length of the collimating system is shorter than an image-side focal length of the image formation system.

According to the present disclosure, it is possible to provide a compact OCT device capable of satisfactorily capturing images of both the anterior segment OCT and the fundus OCT.

DETAILED DESCRIPTION

Figure 1:
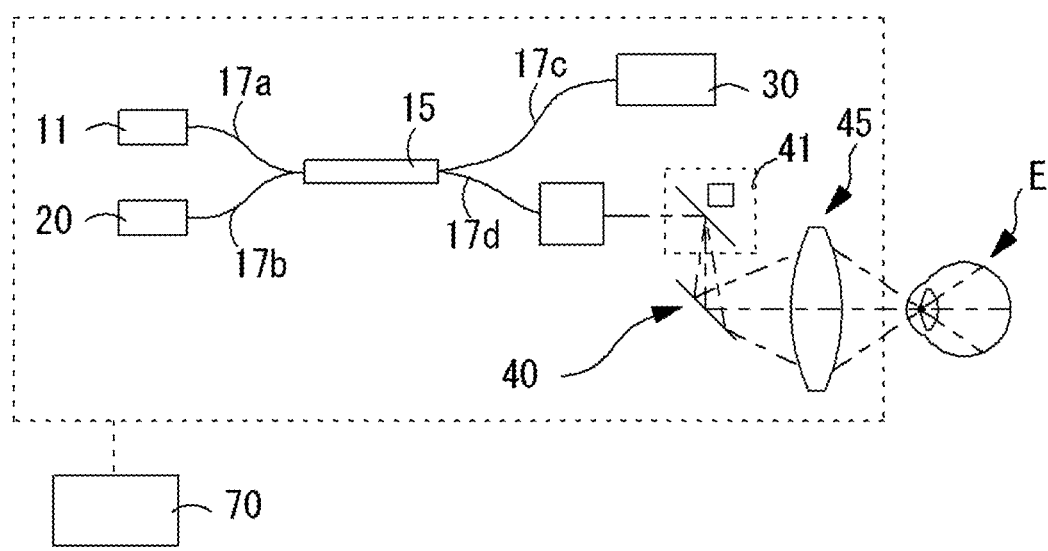
FIG. 1 is a diagram showing an overall configuration of an OCT device.

An exemplary embodiment of an OCT device according to the present disclosure will be described, with reference to the drawings. The OCT device according to the embodiment is an SD-OCT (Spectral-Domain OCT). The OCT device acquires OCT data of a subject eye. In the OCT device of the present embodiment, OCT data of a fundus of the subject eye and OCT data of an anterior segment of the subject eye are selectively captured. As shown in FIG. 1, the OCT device may have a control unit 70, and the control unit 70 may switch an imaging mode between a fundus imaging mode and an anterior segment imaging mode. In the fundus imaging mode, an image of the fundus OCT is captured, and in the anterior segment imaging mode, an image of the anterior segment OCT is captured.

Referring to FIG. 1, a schematic configuration of an optical system of the OCT device according to the present embodiment will be described. As shown in FIG. 1, the OCT device includes an OCT optical system (interference optical system) 100. In addition, the OCT device may include a light guiding optical system 200 and an optical path length adjustment unit.

The OCT optical system 100 according to the embodiment includes at least a spectroscopic optical system 20. In addition, the OCT optical system 100 may include an OCT light source 11, a light splitter 15, and a reference optical system 30. As shown in FIG. 1, each unit is connected through optical fibers 17a to 17d as a light guide path.

The OCT optical system 100 detects a spectral interference signal between reflection light of measurement light irradiated on the subject eye and reference light by the spectroscopic optical system 20. The reflection light is the measurement light reflected from the subject light. The OCT data of the subject eye is acquired (generated) by performing arithmetic processing on the spectral interference signal by the image processor.

The OCT light source 11 of the present embodiment emits low coherent and broadband light. For example, the OCT light source 11 may be an SLD light source, and light, which is emitted from the OCT light source 11, may be near-infrared light. As an example, light, which has a central wavelength of 880 nm, may be illuminated from the OCT light source 11.

The light splitter 15 splits the light emitted from the OCT light source 11 into measurement light and reference light. FIG. 1 shows the light splitter 15 as a fiber coupler. As shown in FIG. 1, the measurement light is irradiated on the subject eye through the light guiding optical system 40. Further, the reflection light of the subject eye reverses through the light guiding optical system 40 to be guided into the spectroscopic optical system 20. The reference light is guided into the spectroscopic optical system 20 through the reference optical system 30. In FIG. 1, the reflection light and the reference light of the measurement light are combined by a coupler (for example, the light splitter 15 in FIG. 1) and then guided into the spectroscopic optical system 20.

As shown in FIG. 1, the light guiding optical system 40 may include an optical scanner 41, an objective optical system 45, and the like. The optical scanner 41 is used to scan the measurement light on the tissue of the subject eye. The measurement light scanned by the optical scanner 41 is scanned on the tissue of the subject eye through the objective optical system 45.

In a case of acquiring the fundus OCT, as shown in FIG. 1, the measurement light passing through the objective optical system 45 may be turned around one point (referred to as a pivot point). The pivot point is disposed in the anterior segment through alignment, and thereby the fundus OCT is acquired.

Figure 2:
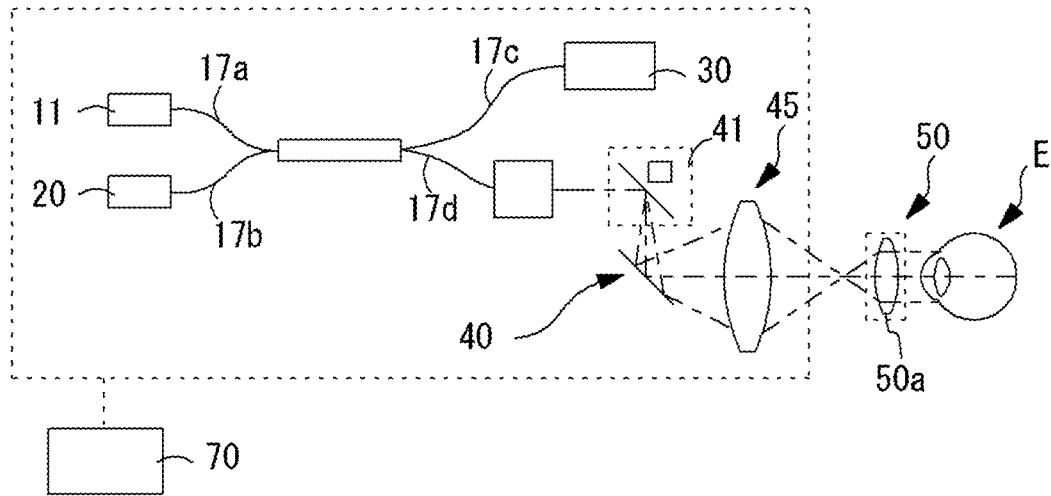
FIG. 2 is a diagram showing an overall configuration in a case of capturing an image of anterior segment OCT.

In a case of acquiring the anterior segment OCT, as shown in FIG. 2, the anterior segment attachment 50 (attachment lens 50a) may be inserted between the objective optical system 45 and the subject eye E. Thereby, a scanning mode of the measurement light may be changed between the case of acquiring the fundus OCT and the case of acquiring the anterior segment OCT. By inserting the attachment lens 50a, the measurement light is irradiated on the telecentric side thereof and the anterior segment OCT is acquired.

The optical path length adjustment unit adjusts an optical path length difference between the measurement light and the reference light. In a case of capturing an image of the fundus OCT, the optical path length difference may be corrected in accordance with an individual difference in an axial length of each subject eye. Further, in a case where an image of the anterior segment OCT is captured, the value may be adjusted to a predetermined value. The optical path length adjustment unit changes an optical path length of at least one of the measurement optical path or the reference optical path. In FIG. 1, the optical path length is changed by moving the emission end of the fiber in the light guiding optical system 40 in the optical axis direction.

<Spectroscopic Optical System>

The spectroscopic optical system 20 of the present embodiment is used as a spectrometer. The spectroscopic optical system 20 spectroscopically detects interference light between the reference light and the reflection light of the measurement light. That is, the spectroscopic optical system 20 spectrally disperses the interference light into frequency components and detects an interference signal for each frequency.

Figure 3:
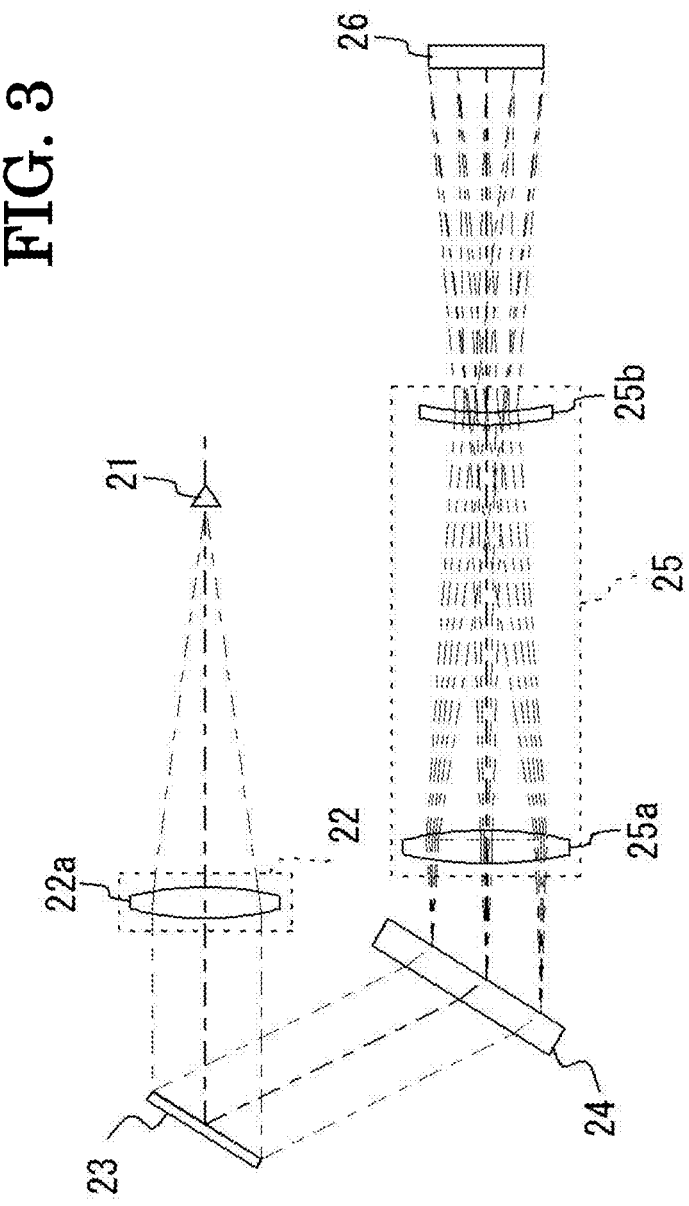
FIG. 3 is a diagram showing a detailed configuration of a spectroscopic optical system.

As shown in FIG. 3, in the present embodiment, the spectroscopic optical system 20 includes a collimating system 22, a grating (spectrally dispersive element) 24, an image formation system 25, and an imaging element (an example of a light receiving element) 26. In addition, the spectroscopic optical system 20 of the present embodiment includes a deflection mirror 23.

However, in the spectroscopic optical system, a mirror for deflecting the optical path does not necessarily have to be disposed. For example, there is an advantage in that the optical path is not deflected in terms of the dimension in the direction intersecting the optical axis.

The combined luminous flux of the reference light and the reflection light of the measurement light is guided into the spectroscopic optical system 20 through the incident end 21. The incident end 21 described herein serves as an apparent point light source for interference light in the spectroscopic optical system 20. For example, the end portion of the fiber 17b can be used as the incident end 21.

The collimating system 22 collimates the interference light illuminated from the incident end 21. In FIG. 3, the incident end 21 is disposed at a focal position (object-side focal position) of the collimating system 22. In FIG. 3, the collimated interference light is deflected by the mirror 23 and illuminated onto the grating 24. In FIG. 3, the collimating system 22 is formed by a lens 22a (collimating lens).

The mirror 23 deflects the interference light at an angle of 90° or more. Thereby, the accommodation size of the spectroscopic optical system 20 is decreased. The mirror 23 is disposed between the collimating system 22 and the grating 24. That is, the interference light is disposed in the collimated region.

The grating 24 spectrally disperses the interference light. As shown in FIG. 3, the grating 24 may be a transmissive optical element (for example, a diffraction grating). However, the grating 24 may be replaced with a reflective optical element. The interference light is separated by the grating 24 in the direction corresponding to the direction in which the pixels are arranged in the imaging element 26.

The spectrally dispersed interference light is incident on the image formation system 25. As a result, the interference light is imaged on the imaging surface through the image formation system 25. In FIG. 3, the image formation system 25 is constituted of two lenses including a lens 25a and a lens 25b. However, the above description is only an example, and various alternative configurations can be adopted for the image formation system 25.

The imaging element 26 is a line sensor (one-dimensional imaging element) in which pixels (elements) are arranged in a one-dimensional direction. The imaging element 26 is disposed on the imaging surface, in other words, at a position at the focal length (image-side focal length) of the image formation system 25.

In the optical paths of the spectroscopic optical system 20, a distance between the collimating system 22 and the grating 24 is regardless of the performance, and therefore can be set to an optional value. Consequently, a total length of the spectroscopic optical system 20 is substantially dominated by a focal length f1 of the collimating system 22 and a focal length f2 of the image formation system 25. In the present embodiment, the device does not include a mechanism for actively changing the focal length f1 of the collimating system 22 and the focal length f2 of the image formation system 25. That is, both f1 and f2 are fixed. That is, in the present embodiment, the conditions of the spectrometer do not change in a case where the fundus OCT and the anterior segment OCT are acquired.

Here, a relationship between the depth resolution in the SD-OCT and the depth range to be image-captured will be described. Unless otherwise specified, the depth range in the present embodiment is a depth to the other end in a case where the zero delay is set as one end of the imaging range. That is, the present embodiment describes values based on an optical system design that does not depend on the full-range technique.

First, the resolution in the depth direction in the OCT can be expressed by the following equation (1).

$$\delta z = \frac{2\ln 2}{\pi} \frac{\lambda_0^2}{n\Delta\lambda} \quad (1)$$

Here, δz indicates the resolution in the depth direction, n indicates the refractive index, and Δλ indicates the total light reception width (full width at half maximum in the spectral distribution).

Further, the imaging range (depth range) in the depth direction can be expressed by the following equations (2) and (3).

$$z_{max} = \frac{N\lambda_0^2}{4\delta\lambda} \quad (2)$$

$$\delta\lambda = ad\lambda \quad (3)$$

$$d\lambda = \frac{\Delta x \cos\theta}{maf_2} \quad (4)$$

Here, zmax is the depth range, N is the number of elements in the imaging element, λ0 is the central wavelength of the measurement light, a is the grating lattice constant, dλ is the sampling wavelength width, Δx is the width of one element in the imaging element, θ is the diffraction angle in the grating, m is the diffraction order, and f2 is the focal length of the image formation system. From the above equations (2) to (4), it can be seen that the depth range zmax is proportional to the focal length f2 of the image formation system. Further, since the depth range zmax is proportional to the number of pixels N and inversely proportional to the one element width Δx, it can be seen that the depth range zmax increases as the number of pixels of the imaging element increases.

Here, in the SD-OCT, the spectrum of the interference light is distributed in one direction on the image plane formed by the image formation system. The width of distribution of the interference light derived from the light source performance is called the source spectrum.

Figure 4A:
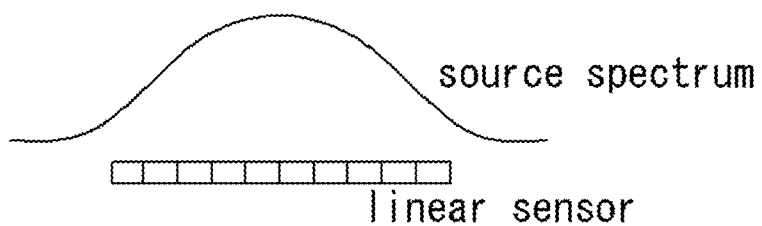
FIG. 4A is a diagram showing a case where a light reception width of an imaging element is narrower than a source spectrum (physical width of spectral distribution derived from a light source).

As shown in FIG. 4A, in a case where the signal range detected by the imaging element is narrow with respect to the source spectrum, the total light reception width Δλ becomes small and the resolution in the depth direction decreases (δz becomes a large value). On the other hand, since the imaging element samples signals in the high density, the sampling width dλ becomes small. Consequently, the depth range zmax is increased.

Figure 4B:
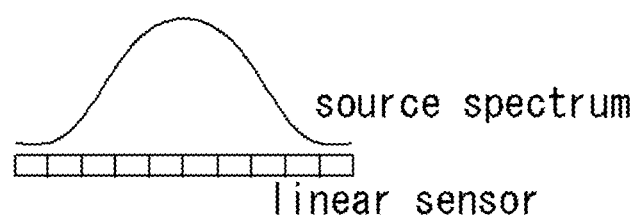
FIG. 4B is a diagram showing a case where the light reception width of the imaging element is balanced with respect to the source spectrum (the physical width of the spectral distribution derived from the light source).

In FIG. 4B, a signal range detected by the imaging element is balanced with respect to a width of the spectral distribution in the source band. Therefore, compared with the case of FIG. 4A, the resolution in the depth direction is improved, but the depth range zmax is narrowed.

As a result of the above-mentioned examination, in order to achieve a wider depth range than the conventional design suitable for the anterior segment OCT while maintaining the resolution (preferably 7 μm or less) suitable for the fundus OCT as in the conventional design, in addition to increasing the number of pixels of the imaging element, it is necessary to sufficiently lengthen the focal length f2 of the image formation system. At that time, since a corneal thickness and an anterior chamber depth are respectively about 0.5 mm and 2 to 3 mm, the depth range capable of imaging from the cornea apex to the anterior capsule of the crystalline lens is preferably 4 mm or more.

By the way, in the spectrometer, it can be considered that the interference light in a spectrally dispersed state is imaged with a finite spot size on the imaging surface. It is considered that the larger the spot size is with respect to the one element width Δx, the more the interference signal for each frequency cannot be decomposed. As a result, the sensitivity is attenuated. In such a case, it is known that the sensitivity more decreases toward the higher frequency region side (that is, at a position farther from the zero delay). The spot size is minimized in a case where the focal length f1 of the collimating system is the same as or longer than the focal length f2 of the image formation system.

On the other hand, in the present embodiment, the focal length f1 of the collimating system 22 is shorter than the focal length f2 of the image formation system 25. That is, f1<f2. Accordingly, the spot size is not minimized.

Meanwhile, the sensitivity attenuation can be expressed as the following equation (5) using the depth range zmax as follows.

$$R(z) = \frac{\pi \sin^2(\pi z / 2z_{max})}{\left(\frac{\pi z}{2z_{max}}\right)^2} \exp\left[-\frac{\pi^2 \omega^2}{8 \ln 2}\left(\frac{z}{z_{max}}\right)^2\right] \quad (5)$$

Here, R(z) indicates sensitivity attenuation, z indicates a depth position, and w indicates an angular frequency.

Figure 5:
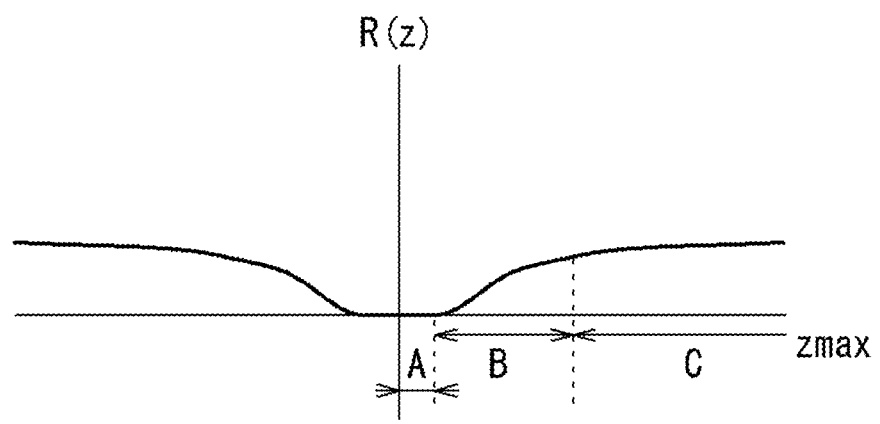
FIG. 5 is a graph showing a relationship between a sensitivity attenuation R(z) and a depth range in the FD-OCT.

As shown in FIG. 5, focusing on the relationship between zmax and R(z), the following features 1) to 3) can be seen for each section.
1) In a section A near an origin, there is almost no change according to zmax.
2) There is a positive correlation between zmax and R(z) in a section B, which has a larger value than the section A. Here, a slope of R(z) turns to a decreasing tendency after passing through an inflection point.
3) In a section C, R(z) is asymptotic to a finite value. The change according to zmax is almost eliminated.

Therefore, sensitivity attenuation is suppressed in a case where the depth range zmax is extended only in a part of the section (section B). Therefore, in the section, it is considered that at least a part of the effect on the sensitivity attenuation caused by the fact that the spot size of the depth range zmax is not minimized can be offset by expanding the depth range zmax.

Figure 6:
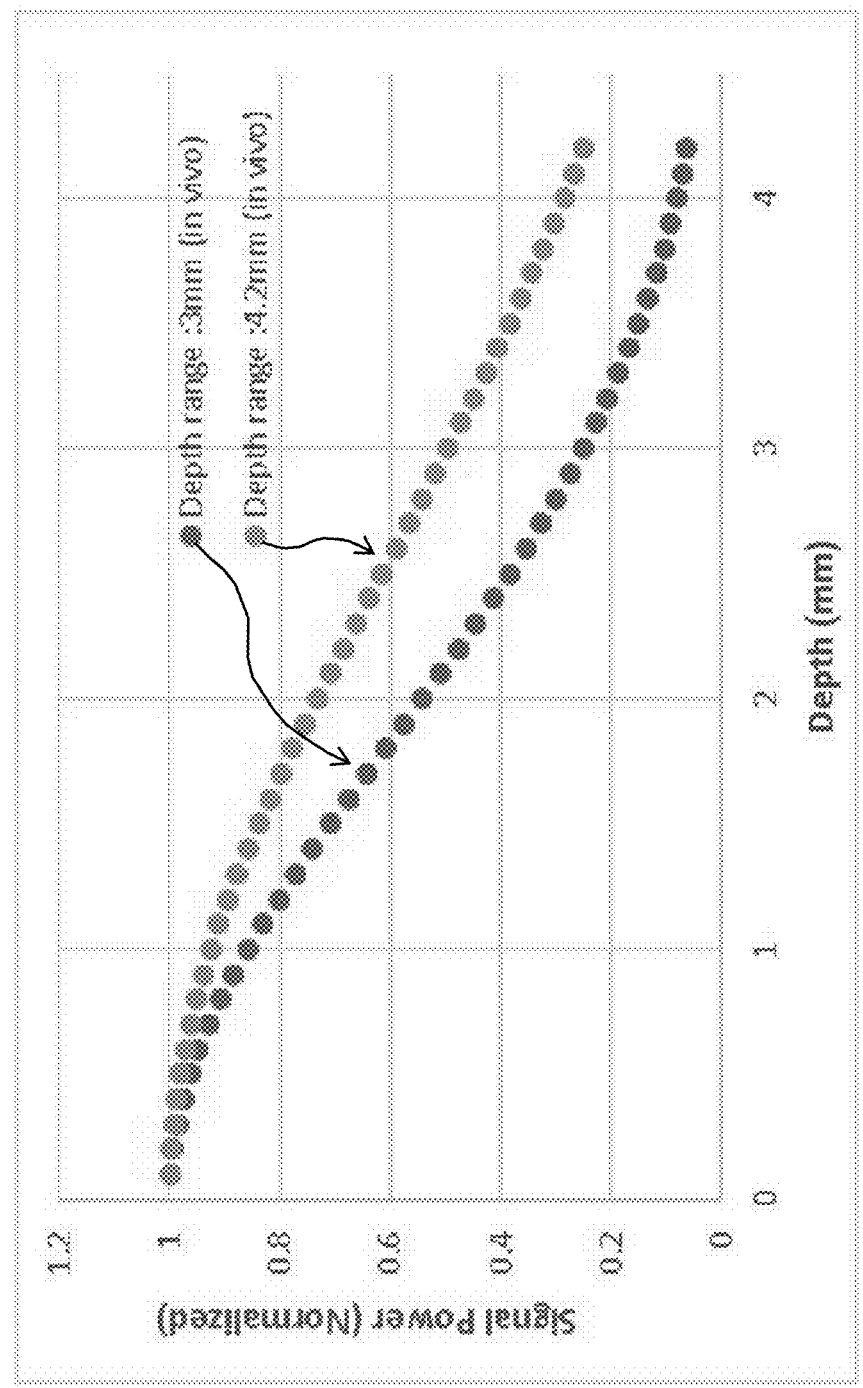
FIG. 6 is a graph showing sensitivity attenuation curves in each case of depth ranges of 3 mm and 4.2 mm.

Next, FIG. 6 shows a sensitivity attenuation curve which is a simulation result based on the expression for two types of the depth ranges of 3 mm and 4.2 mm. Here, each sensitivity attenuation curve in FIG. 6 is premised on a state in which the spot size is minimized.

From FIG. 6, it can be seen that between the depth ranges of 3 mm and 4.2 mm, the larger the depth range, the gentler the slope of the sensitivity attenuation. For example, in FIG. 6, performance at a position of 3 mm in a graph having a depth range of 3 mm is equivalent to performance at 4.2 mm in a graph having a depth range of 4.2 mm.

From the simulation results, it is confirmed that it is possible to receive the full benefit of the effect of suppressing sensitivity attenuation in a case where the depth range is expanded from the conventional SD-OCT range to the range necessary for one-shot imaging from the cornea apex of to the anterior capsule of the crystalline lens. Consequently, since a sensitive margin is created even in a region away from the zero delay, the focal length f1 of the collimating system 22 can be shortened by that amount. As a result, images of both the anterior segment OCT and the fundus OCT can be captured satisfactorily, and a compact OCT device can be implemented.

Here, sensitivity attenuation of the actual device cannot be accurately predicted only by the simulation value. Therefore, in an optical system in which the focal length f1 of the collimating system 22 is shorter than f2 relative to the focal length f2 of the image formation system 25 in a case where the resolution δz of 7 μm or less in the depth direction and the depth range zmax of 4 mm or more are achieved, images of the anterior segment OCT and the fundus OCT were captured, and the effect of sensitivity attenuation is verified. In such a case, f1 is less than a half of f2. More specifically, a ratio of f1:f2 is approximately 1:3. In such a case, the total length of the spectrometer is shortened to the maximum of about 60% as compared with the state where the spot size is minimized.

Figure 7A:
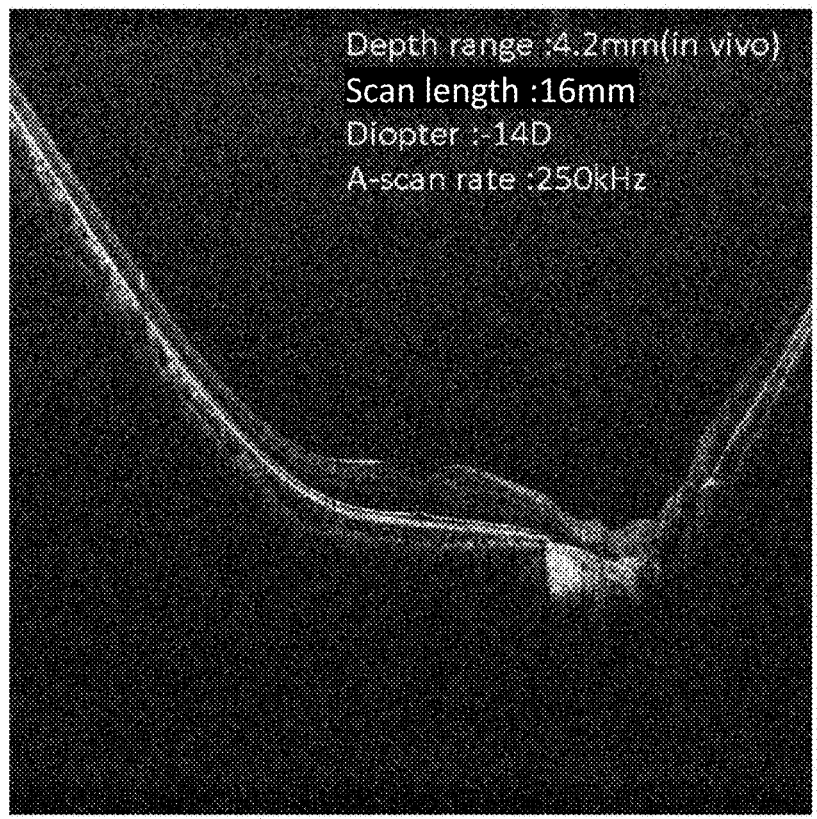
FIG. 7A is a diagram showing a fundus OCT image.
Figure 7B:
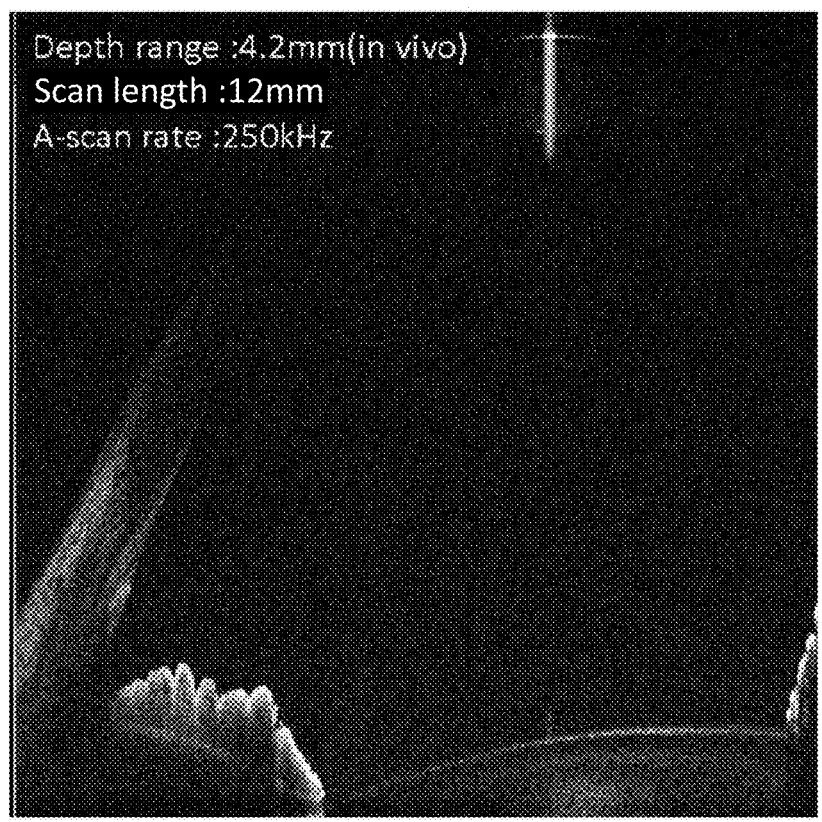
FIG. 7B is a diagram showing an OCT image of an anterior segment.

FIGS. 7A and 7B show the fundus OCT and the anterior segment OCT, respectively.

FIG. 7A shows a B scan of the fundus in a case where a scan length (angle of view) in the transverse direction is 16 mm (approximately, an angle of view of 50°). In the fundus OCT, since the fundus is curved, there is a height difference in the fundus tissue depicted in the B scan in the transverse direction. The height difference varies from individual to a subject eye, and in general, the height difference becomes remarkable in a highly myopic eye or the like. Further, as the scan length (angle of view) in the B scan increases, the height difference tends to occur. Consequently, in the fundus OCT, it is inevitable that a part of the fundus tissue is depicted in the region on the high frequency side (the region away from the zero delay), and the sensitivity attenuation is likely to be regarded as a problem. For example, as shown in FIG. 7A, in a case where the image is captured with central fixation, the central portion of the fundus is depicted at the deepest position. In particular, there is concern about the effect on long-axial length eyes such as highly myopic eyes. However, as a result of the verification, as shown in FIG. 7A, even with a high myopia of −14D, the shape at the central portion of the fundus and the main layer structure from the surface layer of the retina to the surface layer of the choroid layer can be visually identified. However, no problem due to sensitivity attenuation was found.

Further, as shown in FIG. 7B, in the anterior segment OCT, images including the cornea apex, the anterior capsule of the crystalline lens and the chamber angle tissue can be captured in one shot.

As described above, according to the present disclosure, even with a compact spectrometer in which the focal length f1 of the collimating system 22 is shorter than the focal length f2 of the image formation system 25, it is possible to ensure the resolution necessary for fundus OCT while ensuring the imaging range in the depth direction in which images of a plurality of portions in the anterior segment can be captured together.

According to the inventor's estimation from the imaging results of FIGS. 7A and 7B, in a case where a ratio of f1:f2 is in a range of about 1:4, it is considered that the optical system can be reduced while receiving the full benefit of the necessary sensitivity.

<Application of Full-Range Technique>

Further, a full-range technique may be applied to the OCT data. Various methods for removing virtual images in the OCT data are called full-range techniques. In the present embodiment, any full-range technique may be applied, which may allow acquisition of a wider range of OCT data from which virtual images have been selectively removed. In a case where the full-range technique is used, OCT data can be acquired from a region that straddles the zero delay. Therefore, the imaging range in the substantial depth direction can be increased.

As an example of the full-range technique, a technique of removing a virtual image (also referred to as a mirror image) by additional hardware, a technique of correcting by software without using additional hardware, and the like can be mentioned. Further, yet another full-range technique has been proposed as follows. On the basis of a plurality of OCT data pieces having different optical path lengths in a case where detecting the spectral interference signal, at least complementing processing is performed on the overlapping region between the real image and the virtual image in the OCT data, and the OCT data subjected to the complementing processing is obtained. Any of the technologies may be applied in the present embodiment.

<Fixing Method of Optical Elements in Spectroscopic Optical System>

Figure 8:
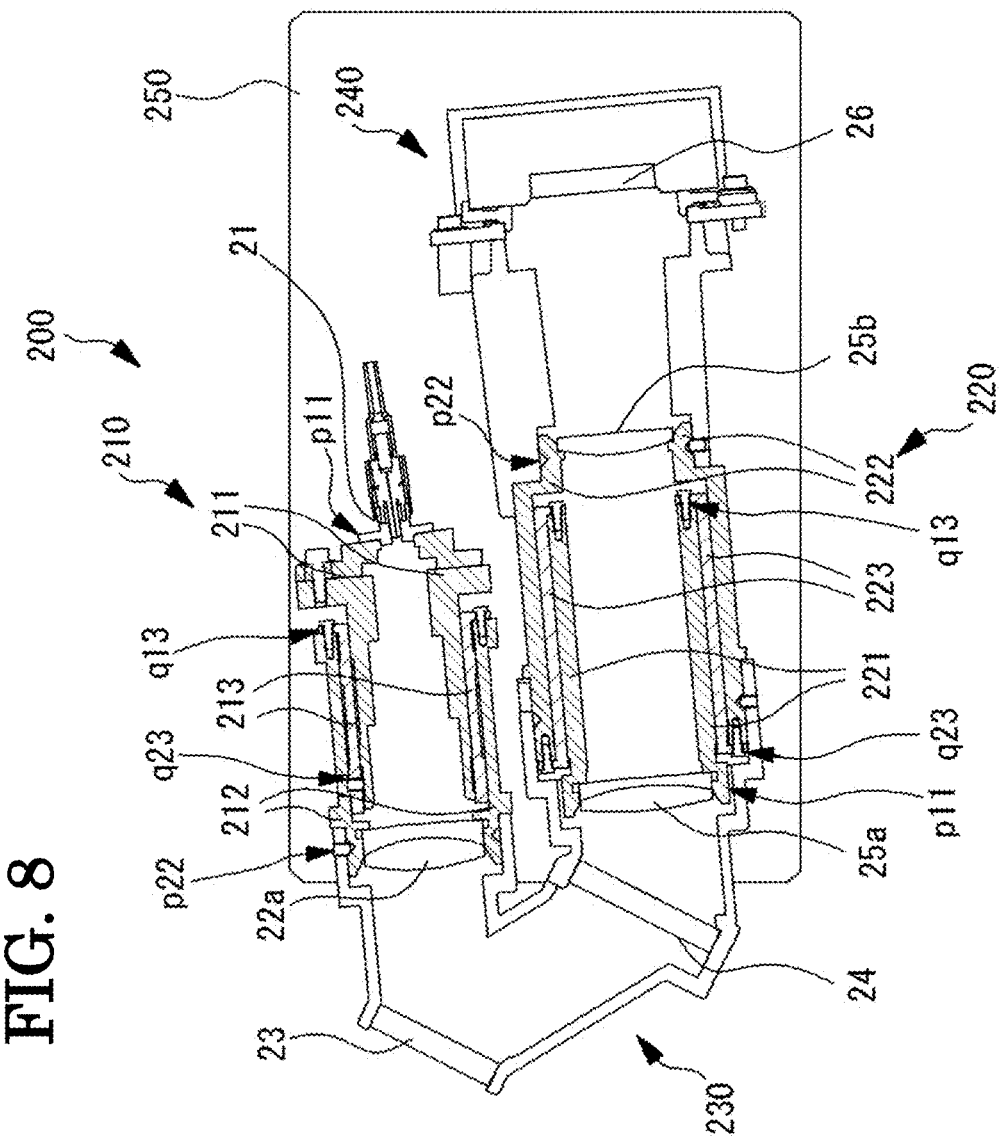
FIG. 8 is a diagram showing a spectroscopic optical system together with a fixing holding unit.

Next, referring to FIGS. 8 and 9, a configuration for fixing and holding the spectroscopic optical system will be described. As shown in FIG. 8, in the present embodiment, the OCT device may include a fixing holding unit 200 that fixes and holds the spectroscopic optical system 20 on a base 250.

In the present embodiment, the fixing holding unit 200 includes at least a first optical mount 210 and a second optical mount 220. The fixing holding unit 200 may additionally include a third optical mount 230 and a fourth optical mount 240.

The first and second optical mounts 210 and 220 each hold at least two of a plurality of optical elements (the incident end 21, the collimating lens 22a, the grating 24, the image forming lenses 25a and 25b, the light receiving element 26) included in the spectroscopic optical system 20. Specifically, one of the first and second optical mounts 210 and 220 holds two adjacent optical elements in the optical axis direction. The first and second optical mounts 210 and 220 each have a configuration for suppressing a change in holding interval of the optical element due to deformation of the mount according to the temperature.

By the way, the spot size of the interference light on the imaging surface is expanded by deviating from the design value in the distance between the respective optical elements. In a case where the distance between the optical elements deviates from the design value, the sensitivity may decrease. Consequently, examination had been performed on the effect on the spot size due to the change in interval between the optical elements, for each combination of adjacent optical elements in the spectroscopic optical system 20. As a result, it was experimentally confirmed that the effect on the spot size increased in the order (descending order) of 1) to 5).

1) The incident end 21 and the collimating lens 22a
2) The image forming lens 25a and the image forming lens 25b
3) The image forming lens 25b and the light receiving element 26
4) The collimating lens 22a and the grating 24
5) The grating 24 and the first image forming lens 25a More specifically, a deviation between 1) and 2) is dominant with respect to the spot size. In the deviation of 3), some effects were seen on the spot size. There was almost no effect on the spot size due to the deviation between 4) and 5).

Consequently, as shown in FIG. 8, in the present embodiment, the first optical mount 210 holds the incident end 21 and the collimating lens 22a. The second optical mount 220 holds the two image forming lenses 25a and 25b.

The first optical mount 210 includes a first member 211 (first holder), a second member 212 (second holder), and a third member 213 (connecting member). The first member 211 holds the incident end 21 (the end portion of the fiber 17b). The second member 212 holds the collimating lens 22a. The third member 213 is fixed onto both the first member 211 and the second member 212.

Likewise, the second optical mount 220 includes a first member 221 (first holder), a second member 222 (second holder), and a third member 223 (connecting member). In the second optical mount 220, the first member 221 holds one of the two lenses 25a and 25b included in the image formation system 25, and the second member 222 holds the other. The third member 223 is fixed onto both the first member 221 and the second member 222.

The first or second optical mount 210 or 220 is formed in an embedded structure which has folded portions B1 and B2 (refer to FIG. 9) at a plurality of locations (two locations in the present embodiment) by the first to third members 211 to 213 or 221 to 223. Thereby, in the first and second optical mounts 210 and 220, displacements of the holding intervals of the two optical elements held by each, that is, displacements due to thermal deformation of the first and second optical mounts 210 and 220 are offset between the first to third members 211 to 213 and 221 to 223 in the thermal deformation of the first to third members 211 to 213 and 221 to 223.

Further, the surfaces of the first to third members 211 to 213 and 221 to 223 that are adjacent to each other (contact) may be formed by lathe machining. By utilizing lathe machining with high machining accuracy, the first to third members 211 to 213 and 221 to 223 can be closely disposed in the first and second optical mounts 210 and 220, and the first and second optical mounts can be disposed closely. As a result, the axial deviation of the two optical elements held by each of the optical mounts 210 and 220 is suppressed.

Figure 9:
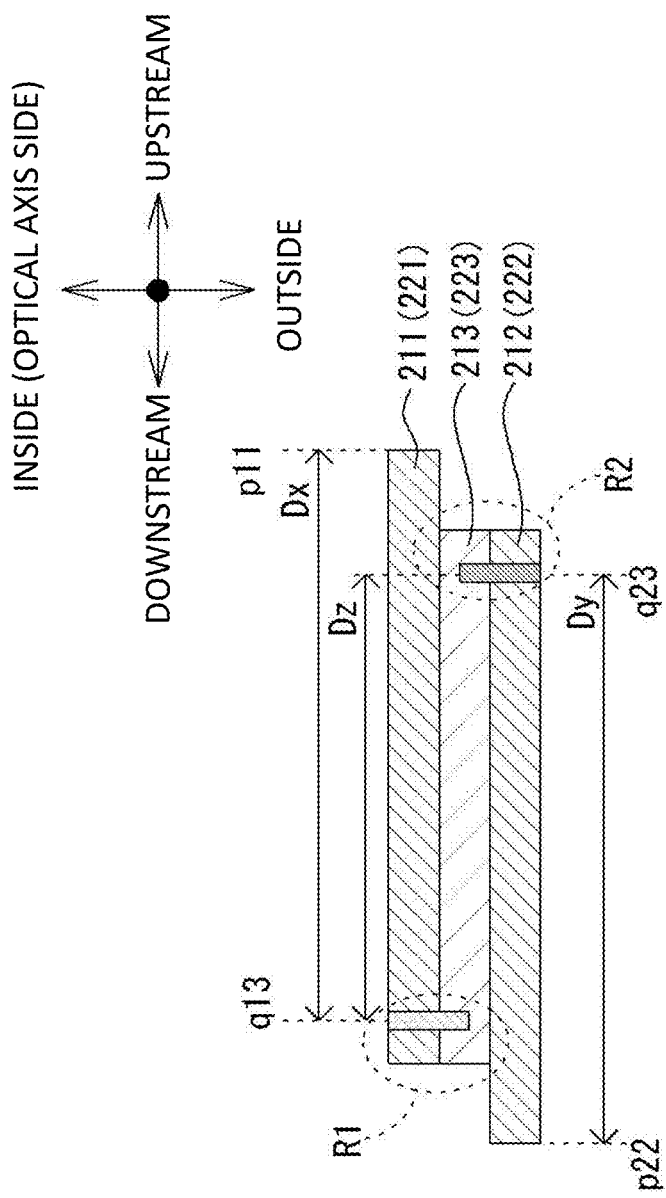
FIG. 9 is a schematic diagram schematically showing a structure of first and second optical mounts.

Referring to FIG. 9, the structures of the first and second optical mounts 210 and 220 will be described in detail. In FIG. 9, the first member 211 or 221 and the third member 213 or 223 are formed so as to extend toward each other along the optical axis from the holding position of the optical element. The second member 212 or 222 is disposed so as to overlap both the first member 211 or 221 and the third member 213 or 223 such that at least a part thereof intersects with the optical axis.

In FIG. 9, the reference p11 indicates a holding position of the optical element in the first member 211 or 221, and p22 indicates a holding position of the optical element in the second member 212 or 222, respectively. Further, the reference q13 indicates a fixed position between the first member 211 or 221 and the second member 212 or 222, and the reference q23 indicates a fixed position between the first member 211 or 221 and the second member 212 or 222, respectively.

As shown in FIG. 9, the fixed position q13 is disposed on the holding position p22 side (in the present embodiment, the downstream side of the spectroscopic optical system 20) of the second member 212 or 222 with respect to the fixed position q23. Around the fixed position q13, the folded portion B1 formed by the first member 211 or 221 and the third member 213 or 223 is formed.

The fixed position q23 is disposed on the holding position p11 side (in the present embodiment, the upstream side of the spectroscopic optical system 20) of the first member 211 or 221 with respect to the fixed position q13. Around the fixed position q23, the folded portion B2 formed by the second member 212 or 222 and the third member 213 or 223 is formed.

In a case where the two members forming the folded portion are viewed from the folded portion, the directions of thermal deformation of the two members are the same. Consequently, in the present embodiment, even in a case where the dimensional changes occur in the first member 211 or 221 and the second member 212 or 222 due to thermal deformation, the same dimensional changes may occur in the third member 213 or 223. In such a case, the holding interval between the two optical elements by the first and second optical mounts 210 and 220 is maintained before and after the temperature change.

Here, a distance from the holding position p11 in the first member 211 or 221 to the fixed position q13 is indicated by Dx, a distance from the holding position p22 in the second member 212 or 222 to the fixed position q23 is indicated by Dy, and a distance between the two fixed positions q13 and q23 in the third member 213 or 223 is indicated by Dz. According to the present embodiment, the dimensions that affect the thermal deformation of the first member 211 or 221, the second member 212 or 222, and the third member 213 or 223 in the optical axis direction are Dx, Dy, and Dz.

Further, the coefficients of thermal expansion in each of the first member 211 or 221, the second member 212 or 222, and the third member 213 or 223 are set to β1, β2, and β3, respectively. Assuming that a margin of error for the change in holding interval of the optical element in a case where the temperature changes from the temperature T to the temperature Ta is E, by using the difference in thermal expansion of each member, a material and Dx, Dy, and Dz of each member are determined to satisfy the following equation (6).

$$|Dx \cdot \beta1(Ta-T) + Dy \cdot \beta2(Ta-T) - Dz \cdot \beta3(Ta-T)| < |E| \qquad (6)$$

That is, in the present embodiment, the material and Dx, Dy, and Dz of each member are determined such that amounts of change in dimensions due to thermal deformation in the first member 211 or 221 and the second member 212 or 222 are approximately equal to amounts of change in dimensions due to thermal deformation in the third member 213 or 223.

As shown in FIG. 9, in a case where Dx, Dy, and Dz are close to each other, the material of each member is selected such that β1<β3 and β2<β3. For example, the first members 211 and 221 and the second members 212 and 222 may be made of the same material (that is, β1=β2). For example, iron may be used for the first members 211 and 221 and the second members 212 and 222, and aluminum may be used for the third members 213 and 223. It is apparent that each member may be a combination of different materials having different coefficients of thermal expansion.

By providing the first and second optical mounts 210 and 220 as described above, it is possible to appropriately suppress the change in distance (change according to the temperature) between the optical elements having a large effect on the spot size of the interference light on the imaging surface of the spectroscopic optical system 20. As a result, the sensitivity performance at each temperature can be appropriately maintained. In particular, as described above, even in a case of adopting an optical design which is disadvantageous in terms of sensitivity that the focal length f1 of the collimating system 22 is shorter than the focal length f2 of the image formation system 25, it is possible to suitably suppress deterioration in sensitivity performance due to the temperature change.

The description will be continued by returning to FIG. 8. In the example of FIG. 8, the first optical mount 210 and the second optical mount 220 are connected to the third optical mount 230. The second optical mount 220 is connected to the fourth optical mount 240 on the downstream side. The third optical mount 230 fixes and holds the mirror 23 and the grating 24. The fourth optical mount 240 fixes and holds the light receiving element 26.

In the present example, in the fixing holding unit 200, each of the third optical mount 230 and the fourth optical mount 240 is directly connected to the base 250 through a screw or the like. At least one of the connection points of the third optical mount 230 and the fourth optical mount 240, a washer or the like absorbs the deformation in a case where the fixing holding unit 200 is deformed by heat. Thereby, it is possible to avoid concentration of mechanical load in a case where the fixing holding unit 200 is deformed due to temperature, and it is possible to suppress deterioration of the optical system.

Although the present disclosure has been described above on the basis of the embodiment, the present disclosure is not limited to the above-mentioned embodiment, and various modifications may be made.

Further, the following OCT devices A1 to A5 are described in the present disclosure.

An OCT device A1 includes:
   an OCT optical system configured to acquire OCT data of a subject eye;
   a spectroscopic optical system provided in the OCT optical system, having a first optical element and a second optical element on an optical path of interference light between reference light and reflection light of measurement light irradiated on the subject eye, and configured to spectroscopically detect the interference light, the reflection light being the measurement light reflected from the subject eye; and
   an optical mount having a first member holding the first optical element, a second member holding the second optical element, and a third member fixed to both the first member and the second member,
   in which the optical mount offsets displacement of a holding interval of the first optical element and the second optical element due to a thermal deformation of the optical mount among the first member, the second member, and the third member in a thermal deformation of the first member, the second member, and the third member.

In an OCT device A2 according to the OCT device A1, the spectroscopic optical system in the OCT device A1 includes:
   an incident end to which the interference light is introduced;
   a collimating lens configured to collimate the interference light illuminated from the incident end;
   a spectrally dispersive element configured to spectrally disperse the collimated interference light for each spectral wavelength;
   an image formation system having two image forming lenses and configured to form an image of the interference light for each spectral wavelength through the two image forming lenses on an imaging surface; and
   a light receiving element disposed on the imaging surface and configured to detect the interference light,
   in which the optical mount holds the incident end and the collimating lens, or the two image forming lenses included in the image formation system, as the first optical element and the second optical element.

An OCT device A3 according to the OCT device A1, includes:
   a first optical mount and a second optical mount separately formed, as the optical mount,
   in which the first optical mount holds the incident end and the collimating lens as the first optical element and the second optical element, and the second optical mount holds the two image forming lenses as the first optical element and the second optical element.

In an OCT device A4 according to the OCT device A1, the first optical element is located upstream of the second optical element in the spectroscopic optical system, and the third member is fixed onto each of the first member and the second member such that a fixed position of the first member and the third member is located downstream of a fixed position of the second member and the third member in the spectroscopic optical system.

In an OCT device A5 according to the OCT device A1, assuming that a tolerance of change in distance between the first optical element and the second optical element in a case where a temperature around the device changes from a temperature T to a temperature Ta is E, and dimensions affecting thermal expansion of the first member, the second member, and the third member in an optical axis direction are Dx, Dy, and Dz, by using a difference in coefficient of thermal expansion, materials of the first member, the second member, and the third member, and the dimensions Dx, Dy, and Dz are determined to obtain the following results:

$$|Dx \cdot \beta 1(Ta-T) + Dy \cdot \beta 2(Ta-T) - Dz \cdot \beta 3(Ta-T)| < |E|.$$

What is claimed is:

1. An OCT device that selectively captures OCT data of a fundus of a subject eye and OCT data of an anterior segment of the subject eye, the OCT device comprising:
    a spectroscopic optical system configured to spectroscopically detect interference light between reference light and reflection light of measurement light irradiated on the subject eye, the reflection light being the measurement light reflected from the subject eye,
    wherein the spectroscopic optical system includes:
        a collimating system configured to collimate the interference light;
        a spectrally dispersive element configured to spectrally disperse the collimated interference light for each spectral wavelength;
        an image formation system configured to form an image of the interference light for each spectral wavelength on an imaging surface; and
        a light receiving element disposed on the imaging surface;
    an object-side focal length of the collimating system is shorter than an image-side focal length of the image formation system; and
    the spectroscopic optical system has the image-side focal length of the image formation system, the image-side focal length being set within a range satisfying a condition that a depth resolution in the OCT data is less than 7 μm and a depth range is greater than a length from a cornea apex to an anterior capsule of a crystalline lens.

2. The OCT device according to claim 1, wherein the collimating system is formed by a collimating lens, and
    the OCT device further comprises an optical mount configured to hold an incident end of the interference light in the spectroscopic optical system and the collimating lens, and to suppress displacement of a holding interval due to a thermal deformation.

3. The OCT device according to claim 1, wherein the image formation system includes two image forming lenses, and
    the OCT device further comprises an optical mount configured to hold the two image forming lenses and to suppress displacement of a holding interval due to a thermal deformation.

4. An OCT device that selectively captures OCT data of a fundus of a subject eye and OCT data of an anterior segment of the subject eye, the OCT device comprising:
    a spectroscopic optical system configured to spectroscopically detect interference light between reference light and reflection light of measurement light irradiated on the subject eye, the reflection light being the measurement light reflected from the subject eye,
    wherein the spectroscopic optical system includes:
        a collimating system configured to collimate the interference light;
        a spectrally dispersive element configured to spectrally disperse the collimated interference light for each spectral wavelength;
        an image formation system configured to form an image of the interference light for each spectral wavelength on an imaging surface; and
        a light receiving element disposed on the imaging surface, an object-side focal length of the collimating system is shorter than an image-side focal length of the image formation system, and
    the object-side focal length of the collimating system is one half or less of the image-side focal length of the image formation system.

5. The OCT device according to claim 4, wherein the object-side focal length of the collimating system is one quarter or more of the image-side focal length of the image formation system.

6. The OCT device according to claim 4, wherein the collimating system is formed by a collimating lens, and
    the OCT device further comprises an optical mount configured to hold an incident end of the interference light in the spectroscopic optical system and the collimating lens, and to suppress displacement of a holding interval due to a thermal deformation.

7. The OCT device according to claim 4, wherein the image formation system includes two image forming lenses, and
    the OCT device further comprises an optical mount configured to hold the two image forming lenses and to suppress displacement of a holding interval due to a thermal deformation.

8. An OCT device that selectively captures OCT data of a fundus of a subject eye and OCT data of an anterior segment of the subject eye, the OCT device comprising:
    a spectroscopic optical system configured to spectroscopically detect interference light between reference light and reflection light of measurement light irradiated on the subject eye, the reflection light being the measurement light reflected from the subject eye,
    wherein the spectroscopic optical system includes:
        a collimating system configured to collimate the interference light;
        a spectrally dispersive element configured to spectrally disperse the collimated interference light for each spectral wavelength;
        an image formation system configured to form an image of the interference light for each spectral wavelength on an imaging surface; and
        a light receiving element disposed on the imaging surface, an object-side focal length of the collimating system is shorter than an image-side focal length of the image formation system, and a mirror that deflects light at an angle of 90° or more is disposed between the collimating system and the spectrally dispersive element.

9. The OCT device according to claim 8, wherein the collimating system is formed by a collimating lens, and the OCT device further comprises an optical mount configured to hold an incident end of the interference light in the spectroscopic optical system and the collimating lens, and to suppress displacement of a holding interval due to a thermal deformation.

10. The OCT device according to claim 8, wherein the image formation system includes two image forming lenses, and the OCT device further comprises an optical mount configured to hold the two image forming lenses and to suppress displacement of a holding interval due to a thermal deformation.

* * * * *